United States Patent [19]

Stanulis

[11] 4,182,33

[45] Jan. 8, 19%

[54] PRESSURE APPLYING DEVICE

[75] Inventor: Nancy U. Stanulis, Marion, Va.

[73] Assignee: Smyth County Dialysis Unit, Marion, Va.

[21] Appl. No.: 865,408

[22] Filed: Dec. 29, 1977

[51] Int. Cl.² ............................................ A61B 17/12
[52] U.S. Cl. .................................... 128/325; 128/327
[58] Field of Search ........... 128/325, 326, 327, 329 R, 128/329 A, 303 R

[56] References Cited

U.S. PATENT DOCUMENTS

| 515,367 | 2/1894 | Rounseville | 128/327 |
|---|---|---|---|
| 1,252,260 | 1/1918 | Gilberg | 128/327 |
| 1,473,041 | 11/1923 | Henderson | 128/327 |
| 2,163,792 | 6/1939 | Littlehales | 128/303 R X |
| 2,571,461 | 10/1951 | Livingston et al. | 128/327 |
| 2,936,759 | 5/1960 | Yuhas | 128/327 |
| 3,050,064 | 8/1962 | Moore et al. | 128/327 |
| 3,570,496 | 3/1971 | Sachs | 128/327 |
| 3,586,001 | 6/1971 | Sanderson | 128/3 |
| 3,954,109 | 5/1976 | Patel | 128/3 |
| 3,977,393 | 8/1976 | Kovacic | 128/327 |
| 4,036,229 | 7/1977 | Marinello | 128/327 |

FOREIGN PATENT DOCUMENTS

| 300256 | 8/1917 | Fed. Rep. of Germany | 128/3 |
|---|---|---|---|
| 12486of | of 1909 | United Kingdom | 128/3 |
| 115789 | 5/1918 | United Kingdom | 128/3 |

Primary Examiner—Richard J. Apley
Attorney, Agent, or Firm—Jones, Thomas & Askew

[57] ABSTRACT

A device which prevents bleeding through need puncture wounds by applying pressure to the wou through an elastomeric appliance having a blunt sk abutting surface held in place over the wound by secuing straps. The pressure applied by the device is sufcient only to prevent bleeding through the wound ai does not impede the subsurface flow of blood.

7 Claims, 7 Drawing Figures

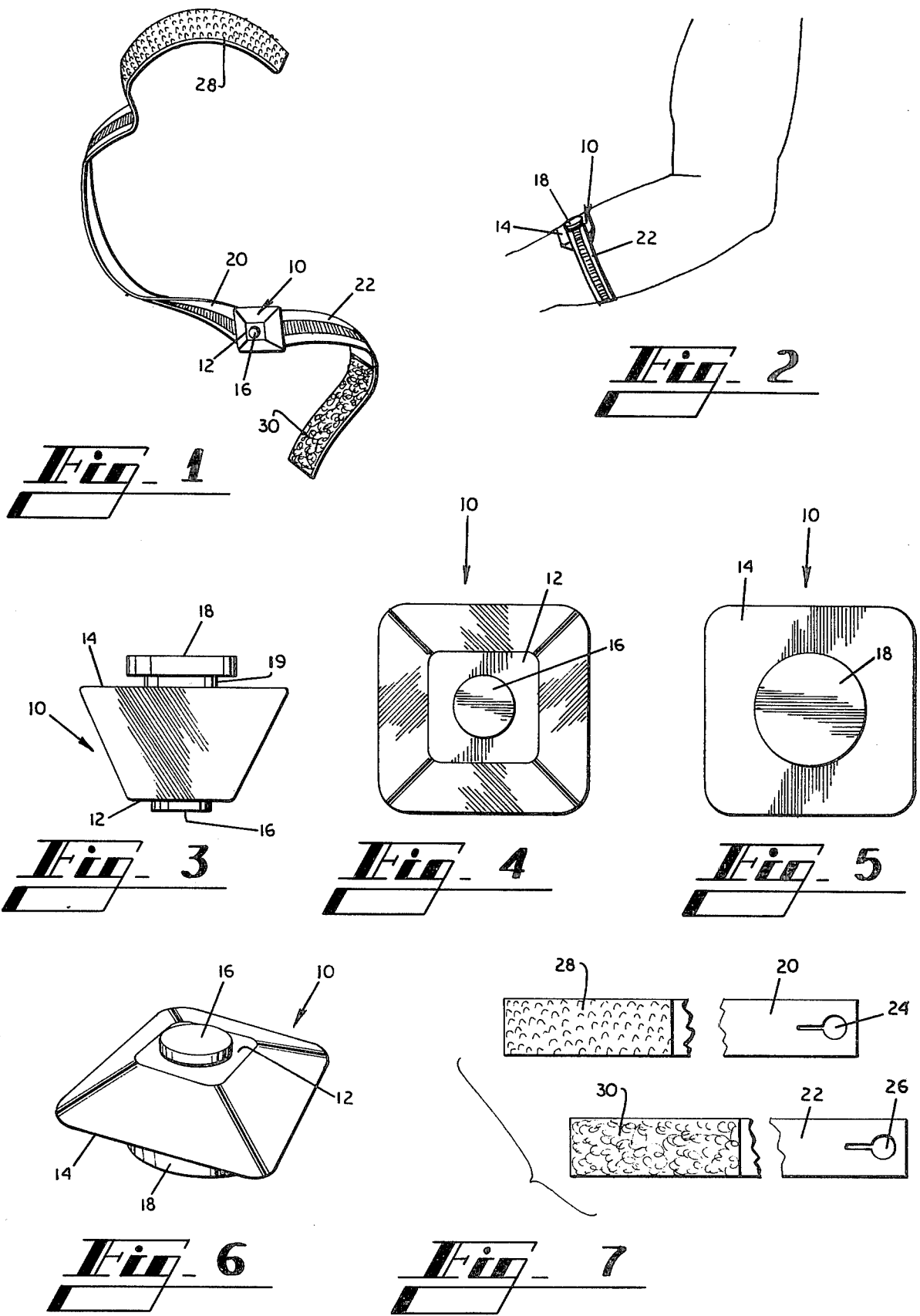

PRESSURE APPLYING DEVICE

This invention relates to a device that may be applied to a needle puncture wound so as to apply sufficient localized pressure to prevent loss of blood through the wound, but not such great pressure as to stop the subsurface flow of blood or to cause tissue damage at the point of application.

People who suffer from kidney dysfunction often depend on dialysis machines to keep them alive. For a certain number of hours per week, a patient must be "hooked-up" to this machine to cleanse his blood of impurities which his own kidneys are no longer able to do. As part of this procedure it is necessary to withdraw blood from the patient's body, cycle the blood through the dialysis machine, and then return the cleansed blood to the patient's body. To facilitate this transfer process, an arteriovenous fistula is created in an extremity of the patient, usually the arm. Such fistula is an artificially created blood pool produced by anastomosing an artery to a vein. This arrangement allows a blood pool suitable for needle puncture for dialysis purposes. After the dialysis procedure is completed, the needles are withdrawn. Due to the size of the needles used in the dialysis procedure, usually ranging from 14-16 gauge or approximately 1/16 of an inch in diameter, and the pooling of the blood in the area of needle insertion, upon withdrawal of the needle it is necessary to apply pressure to the puncture wound in order to prevent loss of blood through the wound.

In the past, this function has usually been performed by a nurse or technician who applies pressure to the wound with his or her thumb until sufficient clotting had occured to prevent bleeding. This process can often take as long as an hour and a half. This is valuable time lost by a highly trained individual who could be attending other patients.

Previous tourniquet-type devices have proved unsatisfactory for this purpose. Since this is a device used on a continuing basis, as opposed to emergency use of tourniquet-type devices, patient comfort is a very important factor. Therefore, devices made from metal, or hard rubber or plastic are inappropriate for this use. Furthermore, continual use of hard materials would cause injury and destruction of tissue in an area that is in a constant healing process. Additionally, tourniquet-type devices are designed to stop the flow of blood through the vein or artery past the point of pressure application by the tourniquet. It is an essential aspect of this invention that subsurface flow of blood not be prevented or restricted. This is accomplished by providing a relatively small pressure-applying area which can cover the wound and be held to press downwardly thereon, while restricting the pressure applied to the skin so as to avoid blocking sub-surface flow of blood.

Accordingly, it is an object of this invention to provide a device which is capable of applying a localized pressure to a point on the body sufficient to prevent bleeding from a wound at that point, but not so great as to prevent subsurface flow of blood or to cause tissue damage.

A further object of this invention is to provide a wound pressure applying device which is comfortable for a patient to wear for extended periods of time and on a continuing basis.

Yet a further object of this invention is to provide a wound pressure applying device that is simple and easy for either a skilled or unskilled person to use.

These and further objects and advantages of the present invention will become apparent from the following detailed description, drawings and claims.

The scope of this invention is not limited to the drawings themselves as the drawings are only for the purpose of illustrating a way in which the principles of this invention can be applied. Other embodiments of the invention utilizing the same or equivalent principles may be used and structural changes may be made as desired by those skilled in the art without departing from the present invention and the purview of the appended claims.

In the drawings:

FIG. 1 is a pictorial view of a disclosed embodiment of a wound pressure applicance according to the present invention;

FIG. 2 is a pictorial view illustrating a typical use of the pressure appliance shown in FIG. 1.

FIG. 3 is a side elevation view of the pressure appliance shown in FIG. 1.

FIG. 4 is a plan view showing the skin contacting surface of the pressure appliance shown in FIG. 1.

FIG. 5 is a plan view showing the attaching surface of the pressure appliance shown in FIG. 1.

FIG. 6 is a pictorial view showing the pressure applying member of the pressure appliance shown in FIG. 1.

FIG. 7 is a top view of the two-piece securing straps.

Referring now specifically to the accompanying drawings wherein like reference numbers designate similar parts throughout the various views shown in FIGS. 1-7, it will be seen that there is a pressure appliance 10 having a truncated pyramid-shaped body attached to Velcro-equipped securing straps 20 and 22 which provide means for securing pressure appliance 10 over the needle puncture wound by wrapping the securing straps around the patient's arm or other limb, as shown in FIG. 2.

Pressure appliance 10 comprises a truncated pyramid-shaped body having a skin contacting surface 12 and an attaching surface 14. Disposed on the skin contacting surface 12 is a pressure applicator 16. The pressure applicator 16 is generally cylindrical in shape, occupying less than the total area of the skin contacting surface 12, and extends generally perpendicularly outward from the skin contacting surface 12.

Disposed on the flat attaching surface 14 are attaching structure which enables the pressure appliance 10 to be connected to the attaching strap or straps. Such attaching structure includes the shaft 19 and the enlarged cap 18 which are generally cylindrical in shape and have a common longitudinal axis. Together, the shaft 19 and cap 18 provide a button-like arrangement to which the securing straps 20 and 22 may be attached through attaching slots 24 and 26 which are formed in the straps.

The pressure appliance 10 is preferably cast in one piece from an elastomeric material such as room temperature vulcanized rubber or the like. In order to avoid injury and destruction of tissue, proper pressure application and patient comfort, such elastomeric material must be sufficiently firm to perform the desired wound-blocking function while not being so firm as to cause unnecessary patient discomfort or skin damage. It has been found that such results are obtained with elastomeric material preferably having hardness of 25 to 35 on the Shore "A" durometer scale.

FIG. 2 illustrates a typical use of the pressure application device. The cap 18 is inserted through the attaching slots 24 and 26 of the securing straps 20 and 22. The pressure appliance 10 is then mounted on the body with skin contacting surface 12 contacting the skin such that pressure applicator 16 is located directly over the needle puncture wound. The securing straps 20 and 22 are then wrapped around the arm of the patient and fastened together by pressing the surface of the Velcro securing strap 20 having nylon hook-type fasteners 28 into contact with the surface of Velcro securing strap 22 having nylon nap-type fasteners 30, thereby securing the pressure appliance 10 in place. The securing straps 20 and 22 need only be adjusted to sufficient tension to securely hold pressure appliance 10 in place. Therefore, pressure appliance 10 and securing straps 20 and 22 do not act as a tourniquet and the subsurface flow of blood is not prevented or reduced while loss of blood through the wound is prevented.

The ability of the pressure appliance to prevent bleeding from a wound without restricting the subsurface flow of blood is due to the "shoulder" effect of skin contacting surface 12. Pressure applicator 16 is disposed on skin contacting surface 12 such that pressure applicator 16 accounts for only a portion of the total area of skin contacting surface 12. In operation, skin contacting surface 12 provides a "shoulder" which effectively limits the degree of indentation produced by pressure applicator 16 beyond the uncontacted skin area by providing a great area over which to distribute the total force exerted by the pressure appliance. Thus, a tourniquet efect is avoided.

It will be readily seen by one skilled in the art that the dimensions of the pressure appliance 10, the pressure applicator 16, and the securing straps 20 and 22 may be varied in order to accomodate varying sized needle puncture wounds and members of the body to which the pressure must be applied. Therefore, it is obvious that the present invention is suceptable of change and modification without departing from the principles and spirit thereof, and for this reason it is to be understood that the present invention is not to be limited to the precise arrangement and formation of the several parts herein shown in carrying out the invention in practice, except as claimed.

What is claimed is:

1. A device capable of applying localized pressure to a selected point on the body so as to prevent the loss of blood from the wound left by a needle puncture, without preventing sub-surface flow of blood, such device comprising:
   a truncated pyramid-shaped appliance of an elastomeric material having a skin contacting surface and an attaching surface;
   a blunt projection protruding from said skin contacting surface with such projection occupying less than the total area of said skin contacting surface;
   attachment means associated with said attaching surface; and
   adjustable fastening means operatively associated with said attachment means, to adjustably secure the appliance in position over wounds in body members of varying sizes, so that said blunt projection blocks the flow of blood from the wound without blocking sub-surface flow of bood in such body member.

2. The device as in claim 1, wherein said elastomeric material has a hardness of 25 to 35 on the Shore "A" durometer scale.

3. The device as in claim 1, wherein said adjustable fastening means comprises two straps, one of which provides nylon hook-type fasteners and the other matching nylon nap-type fasteners.

4. The device as in claim 1, wherein said attachment means comprises two cylinders of different diameter protruding from said attaching surface and having a common longitudinal axis and disposed on said attaching surface such that the cylinder of the smaller diameter is located between said attaching surface and the cylinder of greater diameter.

5. The device as in claim 1, wherein said skin contacting surface surrounding said blunt projection is operative to engage such body member so as to partially absorb the force of said device against the body member and thereby to prevent blocking sub-surface flow of blood.

6. A device capable of applying localized pressure to a selected point on the body so as to prevent the loss of blood from the wound left by a needle puncture, without preventing sub-surface flow of blood, such device comprising:
   an appliance having an elastomeric skin contacting surface and an attaching surface;
   a projection protruding from said skin contacting surface, with said projection having a blunt skin abutting surface which occupies less than the total area of said skin contacting surface;
   attachment means associated with said attaching surface; and
   adjustable fastening means operatively associated with said attachment means to adjustably secure the appliance in position over wounds in body members of varying sizes, so that said blunt projection blocks the flow of blood from the wound without blocking sub-surface flow of blood in such body member.

7. The device as in claim 6, wherein the blunt skin abutting surface occupies less than the total surface area of the skin contacting surface such that said skin contacting surface provides a shoulder so as to limit the force exerted on the skin by said blunt skin abutting surface by restricting the indentation produced by said blunt skin abutting surface beyond uncontacted skin area.

* * * * *